United States Patent
Kubein-Meesenburg et al.

(10) Patent No.: US 6,235,060 B1
(45) Date of Patent: May 22, 2001

(54) ARTIFICIAL JOINT, IN PARTICULAR ENDOPROSTHESIS FOR REPLACING NATURAL JOINTS

(75) Inventors: Dietmar Kubein-Meesenburg, Kreiensen; Hans Naegerl, Gleichen, both of (DE)

(73) Assignee: HJS Gelenk System GmbH, Frankfurt am Main (DE)

(*) Notice: Subject to any disclaimer, the term of this patent is extended or adjusted under 35 U.S.C. 154(b) by 0 days.

(21) Appl. No.: 09/308,047

(22) PCT Filed: Nov. 12, 1997

(86) PCT No.: PCT/EP97/06315

§ 371 Date: Jul. 1, 1999

§ 102(e) Date: Jul. 1, 1999

(87) PCT Pub. No.: WO98/20816

PCT Pub. Date: May 22, 1998

(30) Foreign Application Priority Data

Nov. 13, 1996 (DE) .............................................. 196 46 891

(51) Int. Cl.[7] ........................................................ A61F 2/38
(52) U.S. Cl. .................................. 623/20.31; 623/20.14; 623/18.11
(58) Field of Search .............................. 623/16.11, 18.11, 623/20.14, 20.15, 20.21, 20.23, 20.24, 20.26, 20.27, 20.31, 20.11, 20.12, 20.13

(56) References Cited

U.S. PATENT DOCUMENTS

| | | | |
|---|---|---|---|
| 4,888,021 | * | 12/1989 | Forte et al. . |
| 5,133,758 | * | 7/1992 | Hollister ............................ 623/20.31 |
| 5,203,807 | * | 4/1993 | Evens et al. ....................... 623/20.31 |
| 5,336,267 | * | 8/1994 | Kubein-Meesenburg et al. . |
| 5,507,820 | * | 4/1996 | Pappas . |
| 5,556,432 | * | 9/1996 | Kubein-Meesenburg et al. . |
| 5,738,686 | * | 4/1998 | Kubein-Meesenburg et al. . |
| 5,800,370 | * | 9/1998 | Kubein-Meesenburg et al. . |
| 5,879,390 | * | 3/1999 | Kubein-Meesenburg et al. . |

FOREIGN PATENT DOCUMENTS

| | | | | |
|---|---|---|---|---|
| 4310968 | * | 10/1994 | (DE) ....................................... 623/20 |
| 522822 | * | 1/1993 | (EP) ....................................... 623/20 |
| 94022396 | * | 10/1994 | (WO) ...................................... 623/20 |

* cited by examiner

*Primary Examiner*—Jeffrey A. Smith
(74) *Attorney, Agent, or Firm*—Evenson, McKeown, Edwards & Lenahan, P.L.L.C.

(57) ABSTRACT

The invention concerns an artificial joint, in particular an endoprosthesis for replacing natural joints, comprising at least two artificial joint parts with curved articulation faces, a curved contact line being formed on each of the articulation faces. The curved contact line (L1) of one of the articulation faces is part of an elliptical section contour of a first cylinder (1) or cone having the cylinder radius (R1) or the cone angle ($\alpha 1$). The other contact line (L2) takes the form of a counter track of a second cylinder (2) or second cone having the cylinder radius (R2) or the cone angle ($\alpha 2$) and rolling and/or sliding on the first cylinder (1) or first cone. The articulation faces comprise control faces (F1, F2) formed from a plurality of straight contact lines (B). On one side, these control faces (F1, F2) adjoin the contact lines (L1, L2) opposite one another, and each of the contact lines is the connection line between an instantaneous contact point (K) of the contact lines (L1, L2) and an instantaneous common point (Q) or the instantaneous pole of the respective movement systems in a reference plane (X, Y) or a reference sphere in the moved/unmoved system.

5 Claims, 11 Drawing Sheets

FIG. 11

ARTIFICIAL JOINT, IN PARTICULAR ENDOPROSTHESIS FOR REPLACING NATURAL JOINTS The invention presented relates to an artificial joint, in particular an endoprosthesis for replacing natural joints, comprising at least two artificial joint parts, each with curved articulation faces on which the joint parts articulate with respect to one another.

Such an artificial joint is known from the German patent application P 42 02 717.9. In it, the joint faces have different circular section contours in planes which are perpendicular to each other, namely one longitudinal plane and a transverse plane, where the ratios of curvature for the articulation faces in each of the planes are convex—convex, convex-concave or concave—concave, and the geometry of the joint's articulation faces with respect to one another is determined in each of the two planes by a joint chain with two joint axes, a so-called dimeric joint chain, which runs through the centers of curvature of the articulation faces of their respective section contours. Since the articulation faces of this artificial joint are formed convex-concave, concave—concave or convex—convex, essentially point-like load transmission regions come into being so that increased surface pressures can occur on the articulation faces which lead to wearing away of material. This can shorten the life span of these artificial joints. In order to improve the load transmission between the articulation faces of the parts of the joint, it is suggested in the known joint to arrange a pressure distribution body between each of the individual parts of the joint with which a better and more even distribution of pressure is achieved. However, this pressure distribution body increases the number of required joint parts for the artificial joint.

The object of the invention presented is to create an artificial joint in which point-like load transmission regions are avoided and which it is not necessary to fit with pressure distribution bodies and which at the same time conforms optimally to the conditions of the human body when used as an endoprosthesis, particularly substituting a natural human joint.

According to the invention, this is achieved with an artificial joint of the kind described in the introduction, where on each of the articulation faces a curved contact line is formed, and the curved contact line of one of the articulation faces is part of an elliptical section contour of a first cylinder or a cone having the cylinder radius R1 or respectively the cone angle $\alpha 1$, and the other contact line takes the form of a counter track of a second cylinder or second cone having the cylinder radius R2 or respectively the cone angle $\alpha 2$ and rolling and/or sliding on the first cylinder or first cone; also the articulation faces comprise control faces formed from a plurality of straight contact lines, and, on one side, these control faces adjoin the contact lines opposite one another, and each of the contact lines is the connection line between an instantaneous contact point of the contact lines and an instantaneous reference point of the respective movement systems in a reference plane or on a reference sphere in the moved/unmoved system. In accordance with the invention, a fixed or moving point of the moved or unmoved system will preferably be chosen as reference point, where it is assumed that one of the cylinders or cones is stationary and the other cylinder or cone rolls and/or slides on this stationary cylinder/cone.

The restriction to an unavoidable motion and the choice of the instantaneous axis of rotation as reference point cause, since the holoids roll on each other without sliding, this characteristic to be transmitted to corresponding sections of the control faces. If, instead of the instantaneous center of revolution, another instantaneous common point is used from the reference plane or reference sphere in the moved or unmoved system, the ratio of rolling to gliding can thereby be varied.

According to the invention, it is further provided that the first and the second cylinder or the first and the second cone are arranged with respect to each other so that they form a straight dimeric joint chain or an overlaid dimeric joint chain. For cylinders in a straight dimeric chain, the relationship R=R2+R1 applies or, in an overlaid dimeric chain, the relationship R=R2−R1, where R is the radius of the joint's axial path and R1 the radius of the first cylinder and R2 the radius of the second cylinder. In the case of the cone, analogous to the cylinders, $\alpha=\alpha 2+\alpha 1$ and $\alpha=\alpha 2-\alpha 1$ apply, where $\alpha$ is each of the angles between the axes of the tangential cone pairs.

Since, according to the invention, the cylinders or cones roll or slide on or in each other and the distance between the cylinder axes or the angle between the cone axes remains constant, a flat or spherical dimeric chain results. Thus, the motion, in principle having three parameters and possible as flat or spherical, is limited to two degrees of freedom. The corresponding radii of the cylinder or angles of the cone are preferably adapted to the anatomical conditions of the human knee joint, however can also be changed according to the materials used and their characteristics.

The artificial joint according to the invention distinguishes itself in that a linear load transmission region is formed in every contact position of the articulation faces.

Furthermore, it can be advantageous according to the invention if next to the region of direct load transmission a region without any touching contact is formed in the region of the control faces, such that in action the surrounding tissue is only minimally injured. Therefore, according to the invention it is advantageous if, on the side of the contact lines opposite the control faces, the contact lines are extended arched in bowed lines so as to form toric surfaces. The curved lines are defined in that at the instantaneous contact point of the contact lines in the moved or unmoved system a plane is formed which stretches from the respective contact line of the control faces and the common perpendiculars of the contact lines to a tangent of one of the contact lines at the respective contact point. The toric surfaces are formed such that the outer part of the toric surfaces' articulation faces don't touch each other. These outer parts of the toric surfaces form the curved articulation faces' region of indirect load transmission.

According to the invention, the curved lines are attached to their respective contact lines of the control face without any kink, and their normal lines coincide at the contact point. By advantageously forming the curved lines in circularly arcuate sections—if differently sized radii are chosen in the outer sections—a free space can always be maintained between the articulating toric surfaces during the moving of the articulation faces.

Preferably, the joint according to the invention is used in a four-joint as an endoprosthesis for the human knee such that the medial joint compartment forms the overlaid dimeric chain, and the lateral joint compartment the straight dimeric chain, whereby a four-joint is inevitably formed.

Using the exemplary embodiments shown in the enclosed drawings, the invention will be explained in detail.

According to the present invention, a particular flat or also spherical controlled movement should be achieved. This is achieved in that a flat or spherical linkage is provided. In this linkage, the rotational axes are replaced in a first step by cylinders, arranged around these axes, which touch each other or by circular cones, where these cylinders or cones roll and/or slide on each other. The corresponding radii of the cylinders or the cone angles of the cones are adapted to the anatomical conditions of the natural joint to be replaced, in particular the human knee joint.

Figure 1:
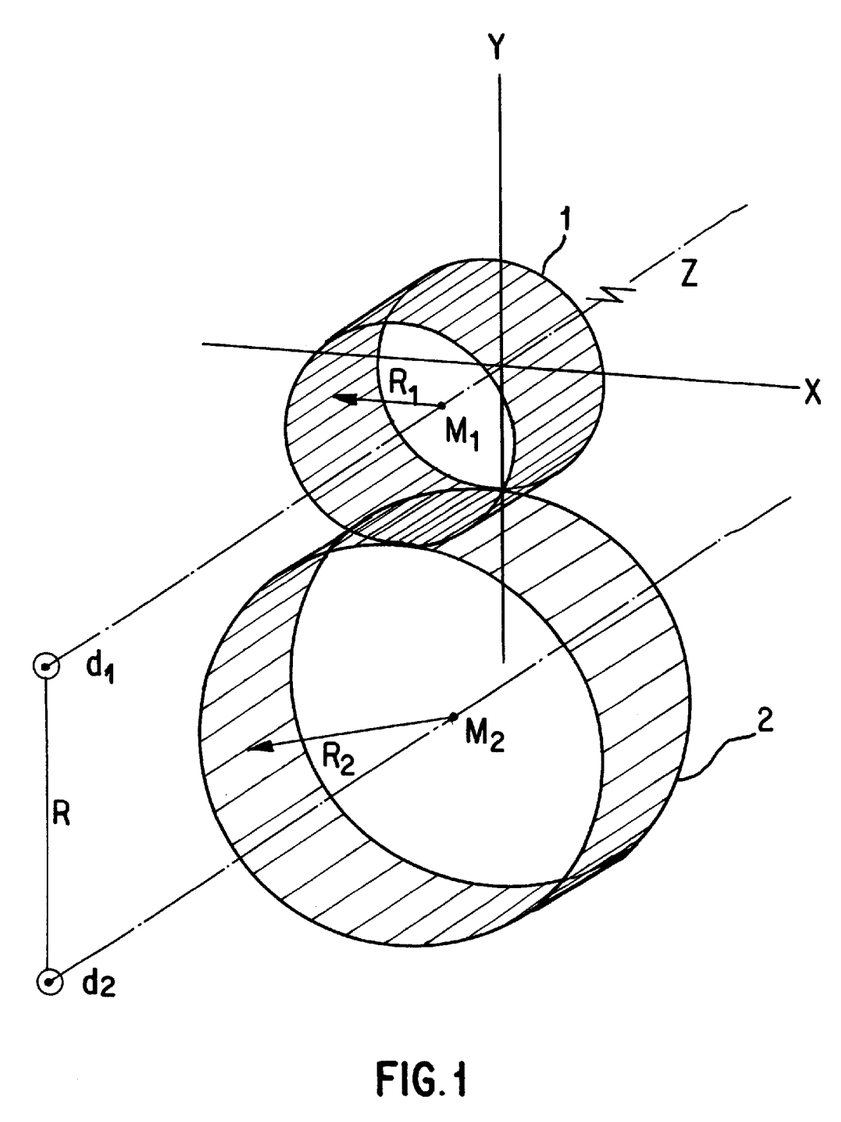
FIG. 1 is a schematic diagram of a joint comprised of two cylinders arranged in a flat, straight dimeric chain.
Figure 1A:
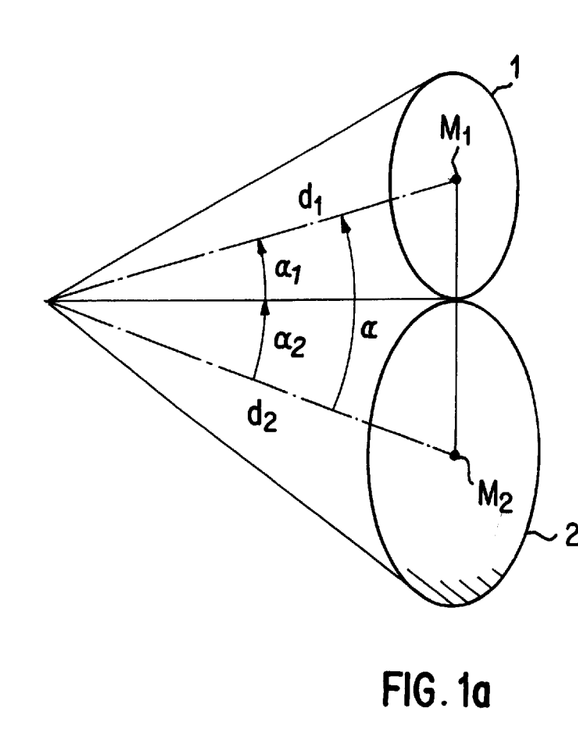
FIG. 1a is a schematic diagram of a joint comprised of two cones rolling on each other in a dimeric joint chain.

In FIG. 1 two cylinders 1, 2 are shown which roll and slide on each other and have the midpoints M1 and M2 and the radii R1 and R2 and the rotational axes D1 and D2. The pair of cylinders shown is arranged as a flat, straight dirneric chain, so that cylinder 2 rolls or slides on cylinder 1. R=R2+R1 applies, where R is the radius of the joint's axial path, also the length of the dimeric joint chain. FIG. 1a shows a representation of two cones 1, 2 rolling on each other and having their respective cone angles α1, α2, where α=α2+α1 applies.

Figure 2:
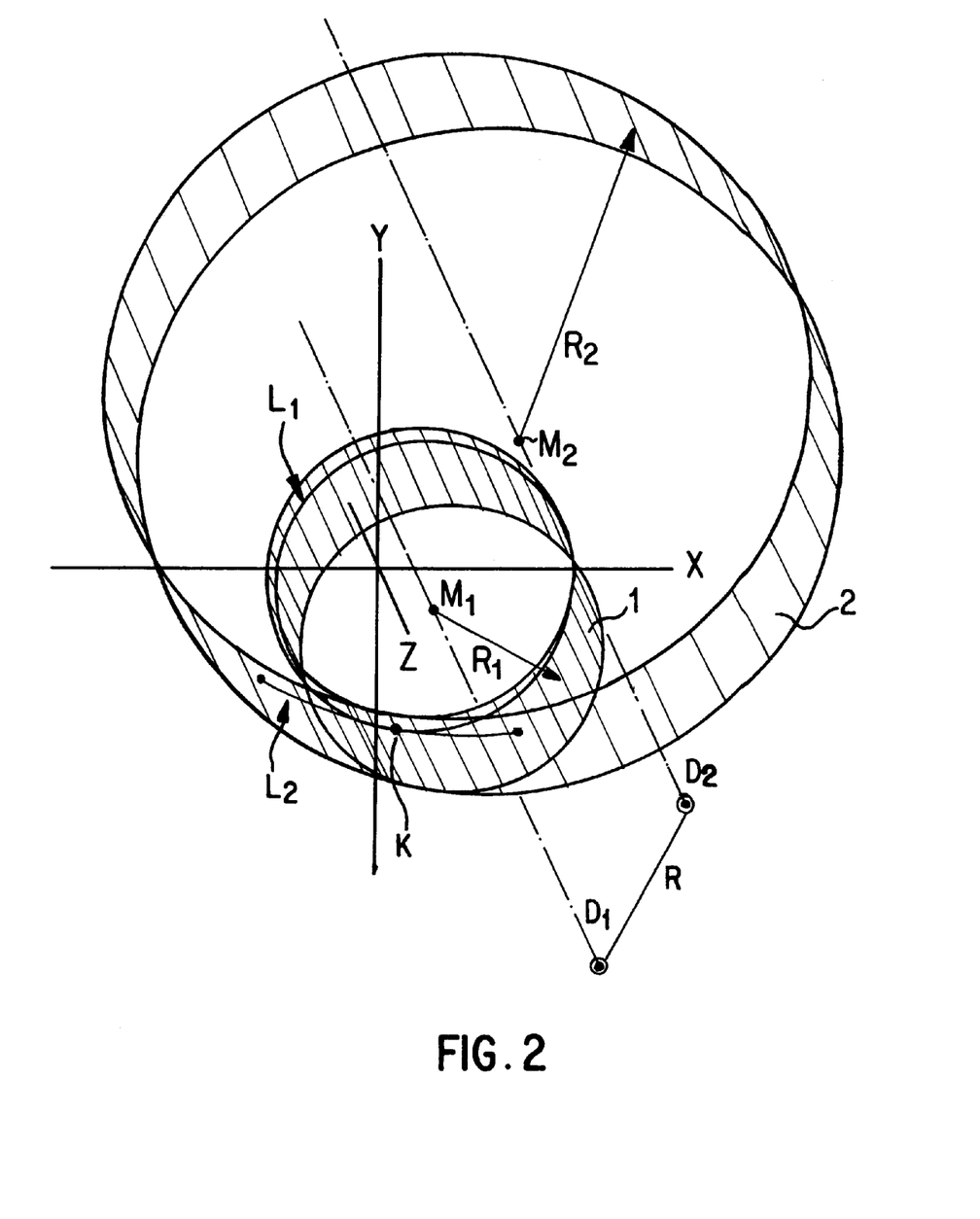
FIG. 2 is a schematic diagram of a joint comprised of two cylinders arranged in an overlaid dimeric joint chain.
Figure 2A:
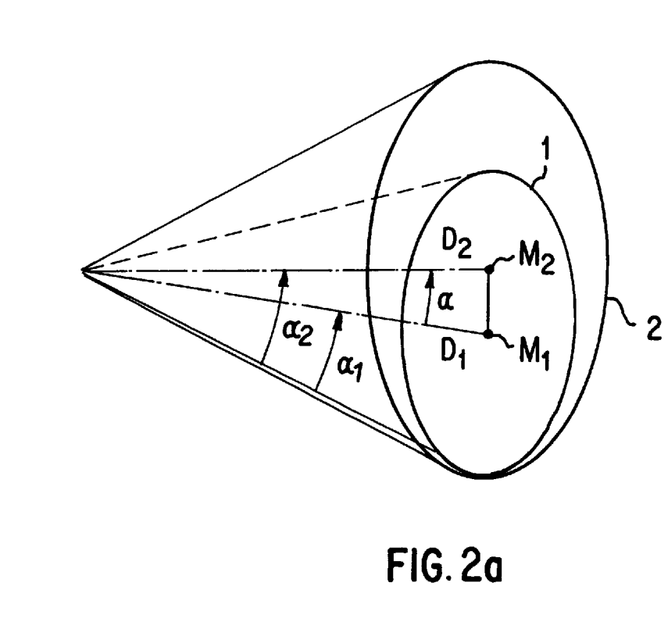
FIG. 2a is a schematic diagram of a joint comprised of two cones rolling one inside the other in an overlaid dimeric joint chain.

In FIG. 2 a cylinder arrangement is shown of cylinders 1 and 2, midpoints M1 and M2, radii R1 and R2 and cylinder axes D1 and D2, where these cylinders are arranged in the form of an overlaid dimeric chain. Here, R=R2—R1 applies, where R is again the radius of the joint's axial path and therefore the length of the dimeric chain. FIG. 2a shows a representation of two cones 1, 2 rolling inside each other and having their respective cone angles α1, α2, where α=α2−α1 is.

Figure 3:
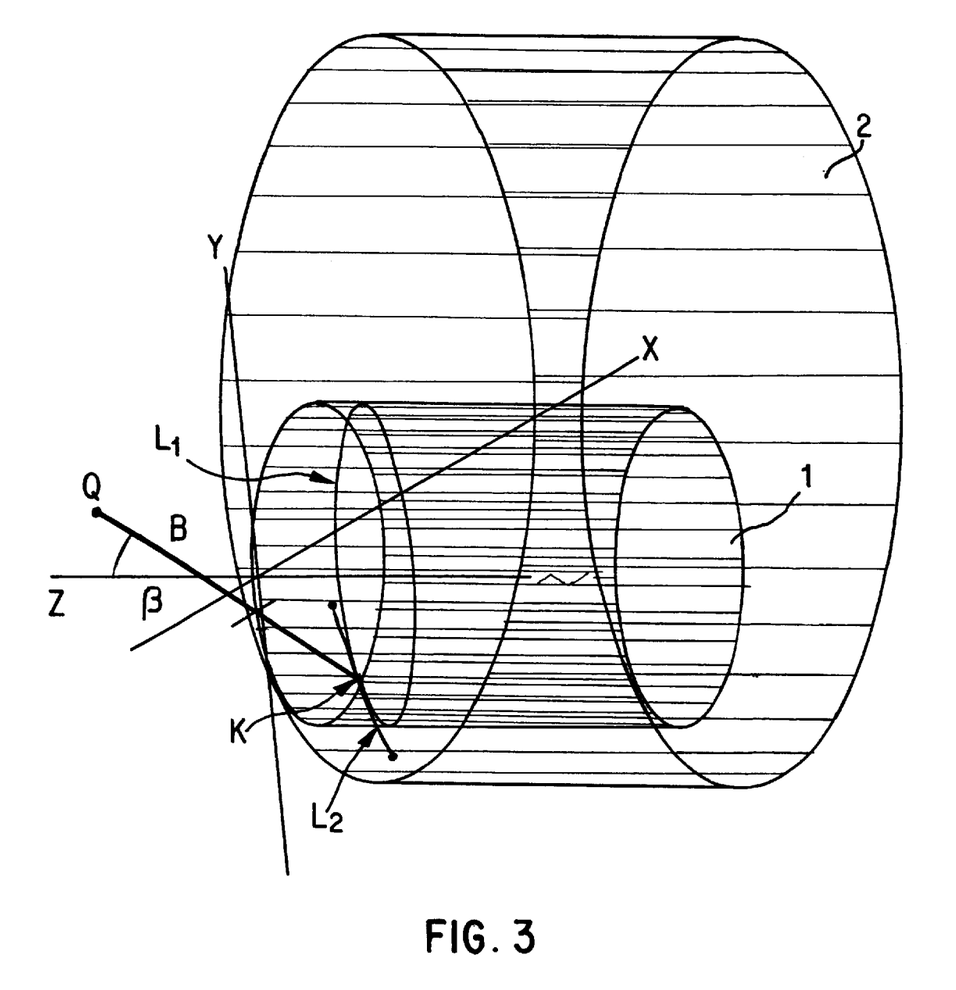
FIG. 3 is a diagram showing the generation of control faces in the joint arrangement of FIG. 2.

As shown in FIG. 3, in this arrangement, for example, cylinder 1 is chosen as the stationary piece, where, by cutting through cylinder 1 at an angle, a contact line L1 is chosen on cylinder 1 which thus has an elliptical form. Cylinder 2 is chosen as the moving piece and rolls and/or slides now on cylinder 1, where on the cylinder surface a counter-curve forms as contact line L2 as a function of the rolling and sliding motion of cylinder 2. This contact line 2 has a arcuated form, seen section-wise. Therefore, both contact lines L1 and L2 have at any given instant a common contact point K. According to the invention, cylinder 1 can, for instance, be assigned as the femural joint piece of the inventive knee in the construction of an artificial joint, and cylinder 2 as the tibial joint part.

Figure 4:
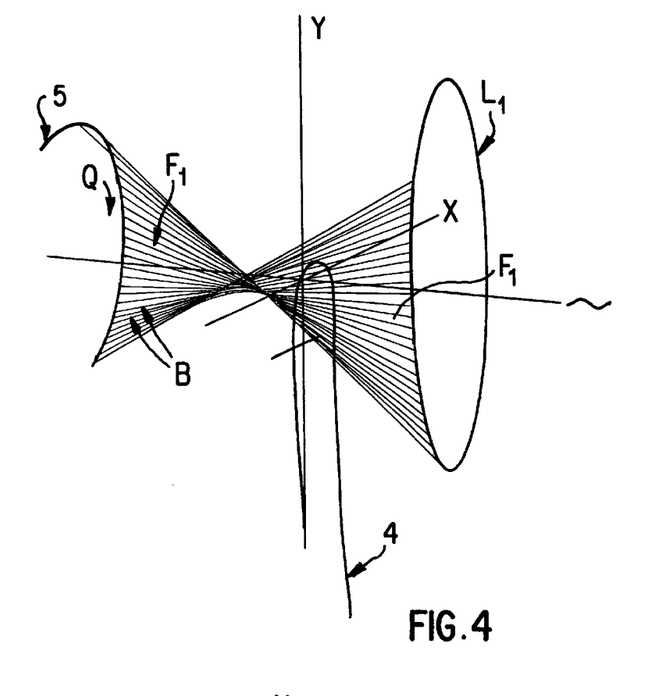
FIG. 4 shows the control face F1 produced by the sum of the contact lines B in a resting system.
Figure 5:
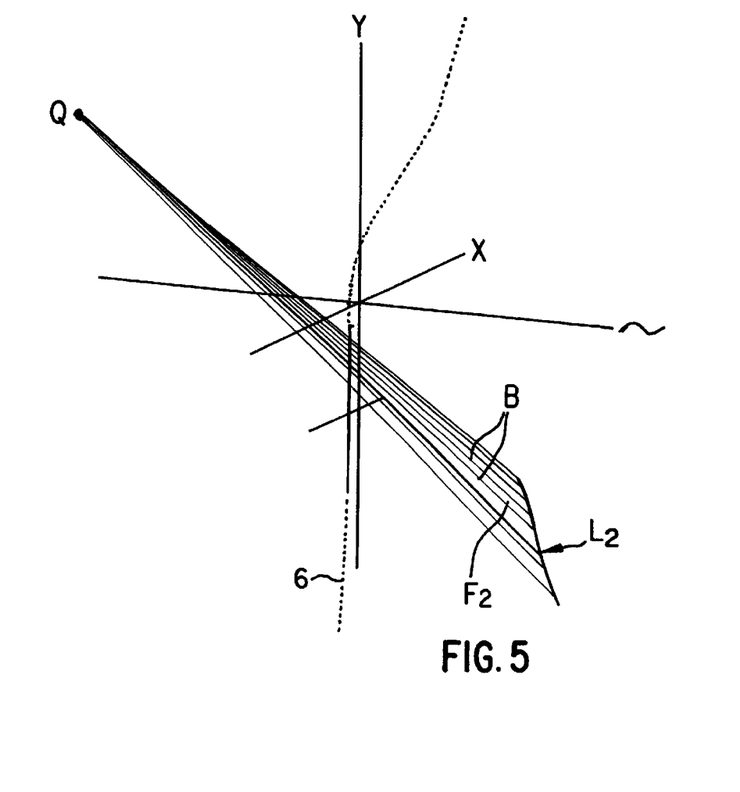
FIG. 5 shows the control face F2 produced by the sum of the contact lines B in a moving system.

In FIG. 3 it is shown how now, in the joint arrangement according to FIG. 2, based on contact lines L1 and L2, which are formed on cylinders 1 and 2, contact lines B, which require linear contact, are produced for generating control faces according to the invention. Here, a basis point Q is advantageously fixed in the moved system, being randomly chosen in a reference plane (sagittal plane) that is shifted to the interior of the joint such that at the instantaneous contact point K of the contact lines L1 and L2 the connection line B advantageously forms an angle β (35°<β<70°) with respect to the z axis. This reference plane lies parallel to the functional plane, here represented by the coordinate plane x and y. The sum of the contact lines B in the resting system produces a control face F1 having lines running between contact line L1 and path 5 of the basis point Q (see FIG. 4). In the moved system, a control face F2 arises between contact line L2 and basis point Q, stationary in this system (see FIG. 5). Therefore, in every state of motion, both control faces F1 and F2 each move linearly in accordance with their design. For each of the joint surfaces a part of the control faces F1 and F2 is chosen which adjoins L1 or L2 and extends a maximum of 3 cm, measured from the contact line to the middle. These parts of the control faces F1 and F2 formed by the contact lines B belong to the region of direct load transmission.

Figure 6:
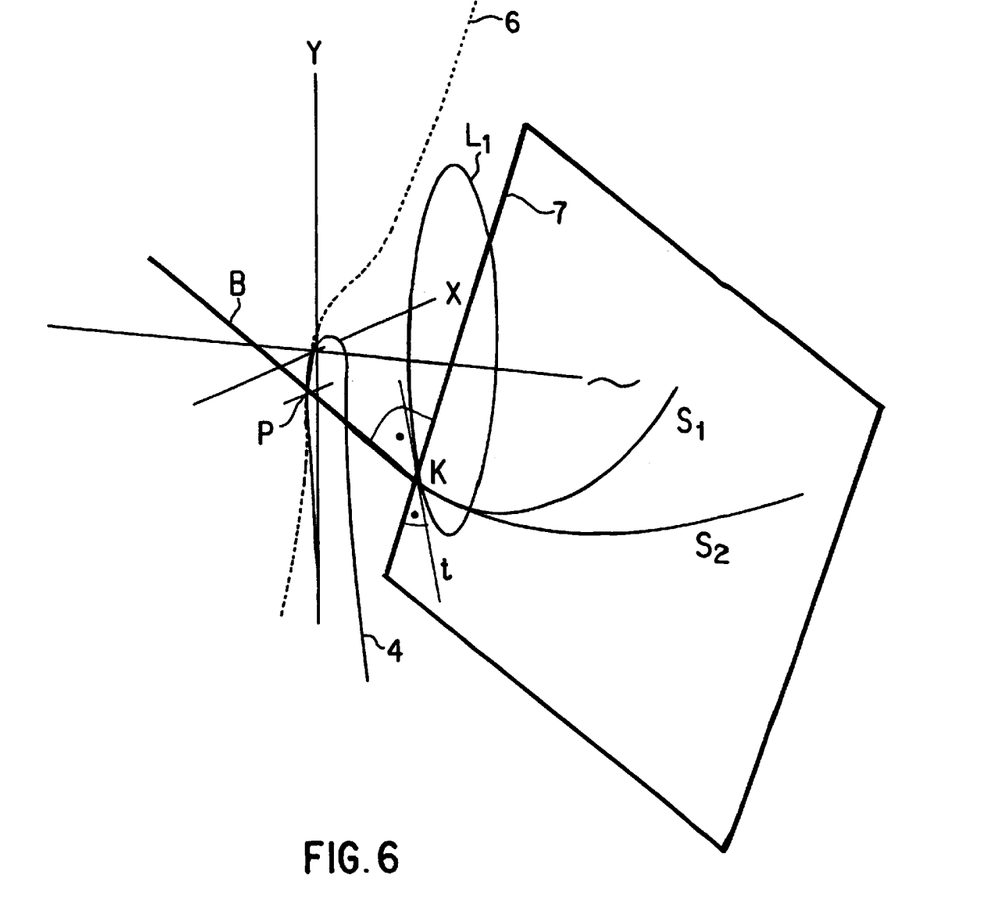
FIG. 6 is a diagram illustrating the construction required for production of articulating partial faces according to the invention.
Figure 7:
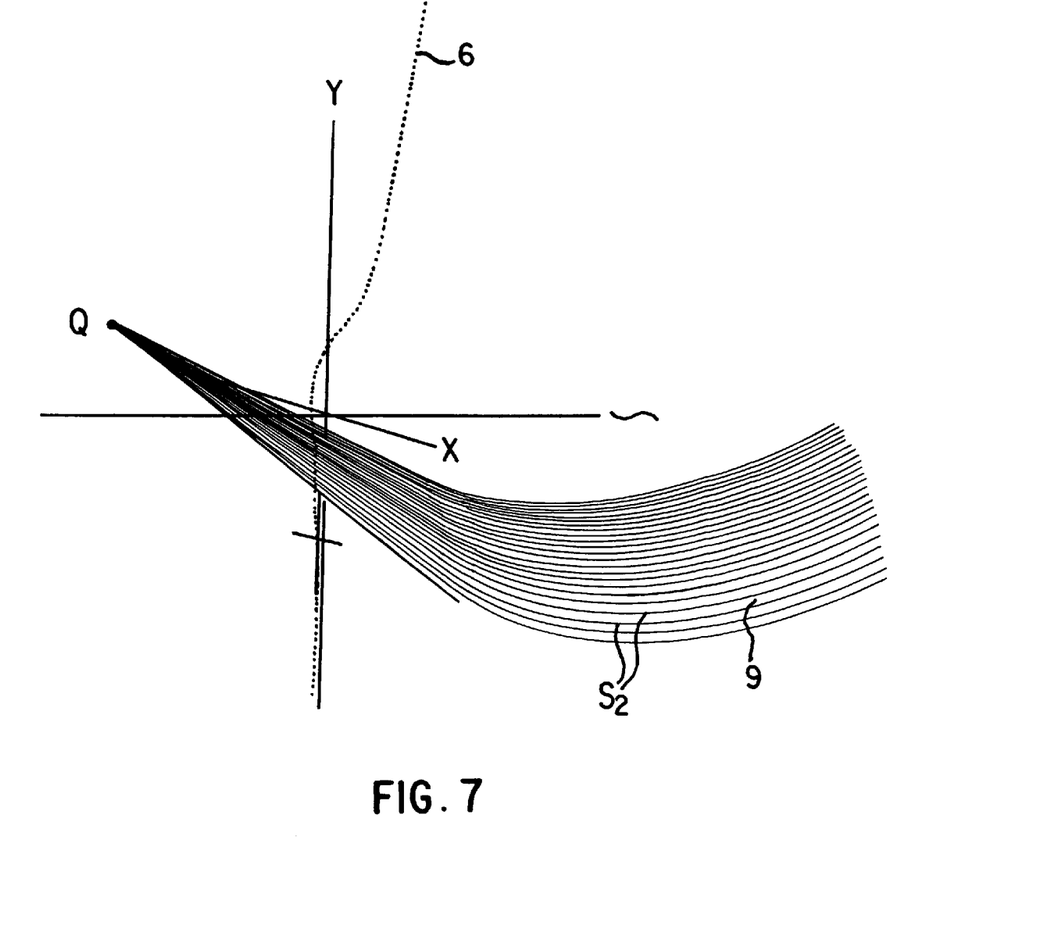
FIG. 7 is an illustration of an articulating toric surface generated by a curved extension of the contact line B in the moved system.
Figure 8:
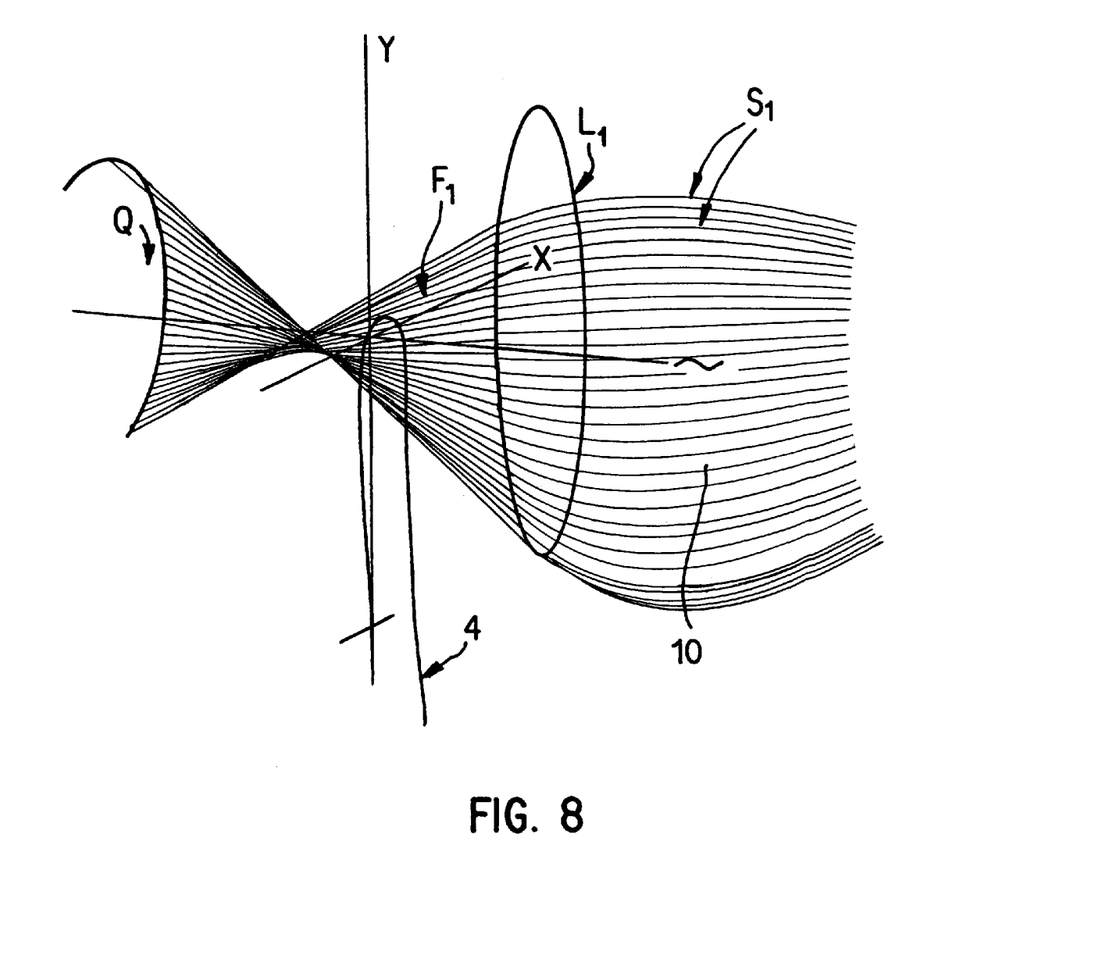
FIG. 8 is an illustration of an articulating toric surface generated by a curved extension of the contact line B in the unmoved system.

Furthermore, it is provided according to the invention that articulating partial faces with indirect load transmission are produced on the side of the contact lines L1, L2 opposite the control faces F1, F2. The design required for that and in accordance with the invention is explained using FIG. 6. At the instantaneous contact point K of the contact lines L1, L2, an instantaneous plane is set up as an aide in the moved and the unmoved system and stretches from the contact line B of the control faces F1, F2 and a common perpendicular 7 of the contact line B and a tangent t of the contact line L1 and/or L2. In this plane, arcuate curves, curved lines S1, S2, which advantageously remain the same throughout their progression, are attached without any kink to the contact line B of the control faces F1, F2. In the moved system, as is shown in FIG. 7, and in the unmoved system, as is shown in FIG. 8, toric surfaces 9, 10 are thereby produced which are attached to their respective control faces F1, F2 without any kink and whose normal lines coincide at the contact point. The arcuate curves S are made such that during motion free space always remains between the articulating toric surfaces 9, 10 which they form. This can be achieved with the circular bowed lines S1, S2 by choosing different sized radii. Furthermore, it can be advantageous to provide S1 and S2 with a common radius over a certain distance (up to maximum 2 cm) and only then, without any kink, to introduce differently sized radii. The region of direct load transmission is thereby extended into the arcuate region. Since the control faces F1 and F2 and the toric articulation faces 10, 9 come about due to the motion of an elliptical section contour comprised of lines and curves, these faces can be produced using a CNC grinding machine. Basis point Q can also be defined in the unmoved system. It can further be advantageous to choose Q depending on the motion and particularly to use for this the instantaneous center of revolution P (FIG. 6) which lies in a random intermediate plane. The control face F1 lies, then, between contact line L1 and the resting pole path 4, and the control face F2 lies between contact line L2 and the moving pole path 6. Resting pole path 4 and moving pole path 6 arise as intersection lines of this randomly chosen plane with the sum of the instantaneous rotational axes of the motion. If the instantaneous center of revolution is chosen to produce the contact lines B, sliding is minimized on the formed control faces F1 and F2 since the holoid surfaces roll on each other. If, instead of the instantaneous center of revolution, another instantaneous common point in a reference plane in the moved/unmoved system is used, the ratio of rolling and sliding can be varied.

Figure 9:
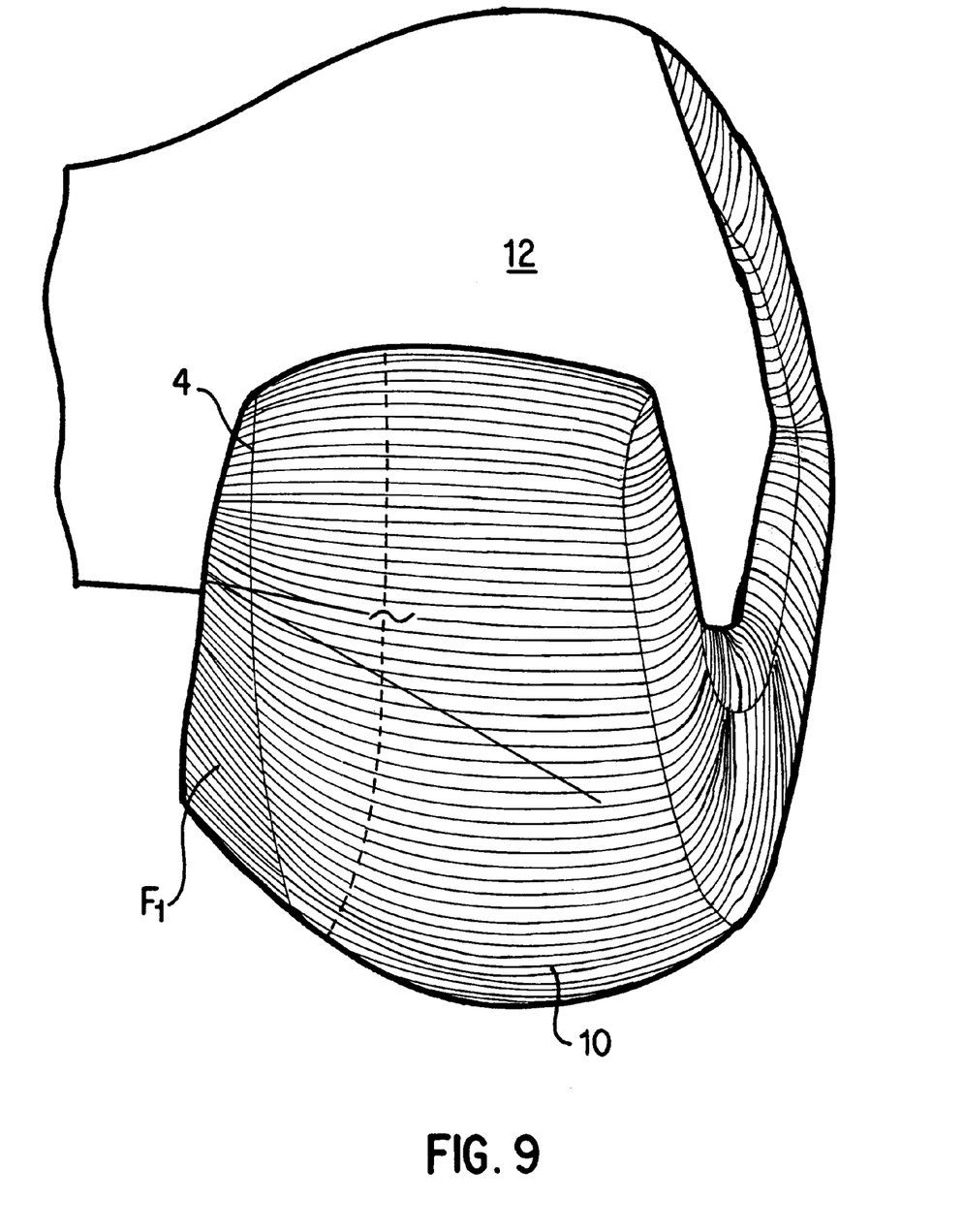
FIG. 9 shows the articulation surfaces of a joint head of an artificial joint incorporating the control surface F1 of the unremoved system with the connected toric surface 10 according to FIG. 8.

FIG. 9 shows the transfer of the unmoved system's configuration from the control face F1 with attached toric surface 10 according to FIG. 8 to an artificial joint part 12 which can form the articulation face of a joint's head. It is to be noted here that the dimensions of the faces F1 and 10 are adapted to the anatomical conditions.

Figure 10:
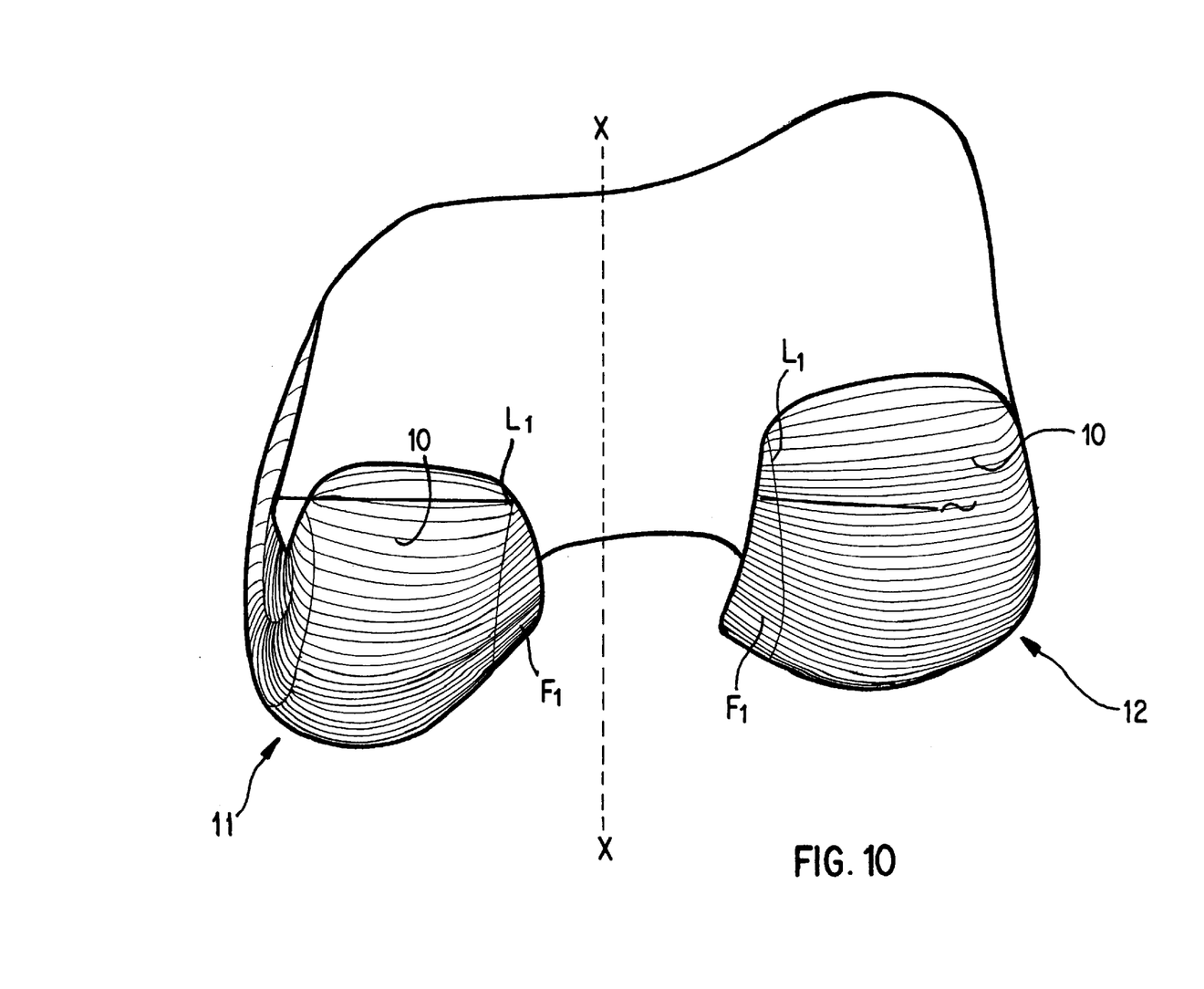
FIG. 10 shows the femoral articulation surfaces of a joint head of an artificial joint incorporating the two control sufaces F1 of the unmoved system with connected toric sufaces 10 according to FIG. 8 on opposite sides of a mid-plane X—X.
Figure 11:
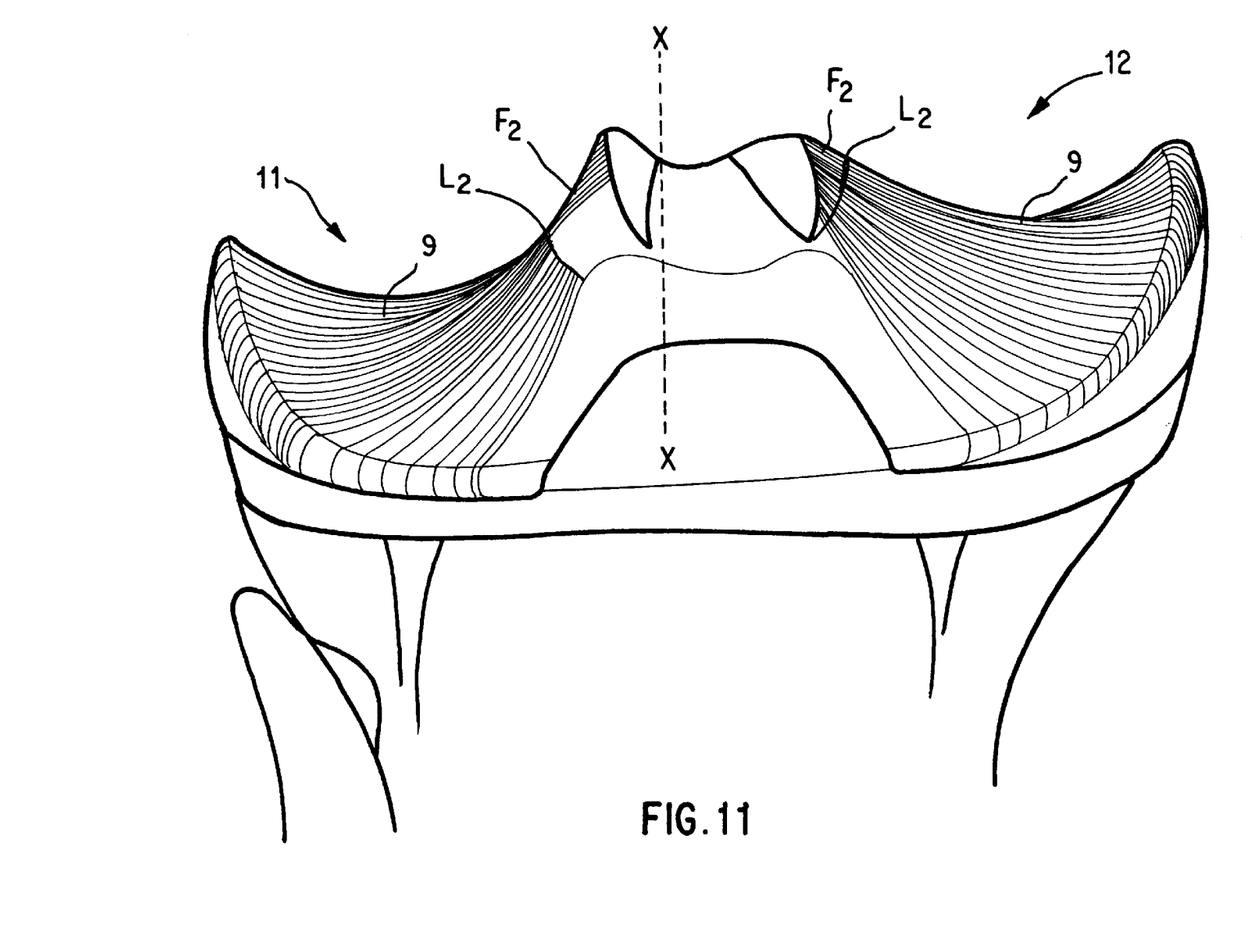
FIG. 11 shows the tibial articulation surfaces of a joint head of an artificial joint incorporating the two control surfaces F2 of the moved system with connected toric surfaces 9 according to FIG. 7 on opposite sides of a mid-plane X—X.

A joint according to the invention is formed advantageously as an endoprosthesis for replacing the human knee joint from by coupling two joint arrangements according to the invention as shown in FIGS. 1 and 2. Here, the control faces of each pair of joint bodies are arranged with respect to a mid-plane X—X such that they lie on the side facing the mid-plane X—X. The tibial joint body and the femoral joint body here are each fixed immovably with regard to each other. Thus, a compulsory characteristic arises which is determined by the resultant four-joint. In the side view the instantaneous center of revolution results as an intersecting point of the lateral and medial chain (or their extensions). In all, the resting pole path is created in the stationary plane and the moving pole path is created in the moved plane. For a knee joint of the right knee seen from behind, FIGS. 10 and 11 show the femoral articulation faces and tibial articulation faces of the lateral joint compartment 11 and the medial joint compartment 12 which are produced according to the design process in accordance with the invention. In the regions of the indirect load transmission, that is the toric articulation faces 9, 10, the radii are chosen such that tibial sized radii are provided for femurs. In the lateral joint compartment 11, an arrangement according to FIG. 2 is formed, namely a straight dimeric joint chain, and in the medial joint compartment 12 an overlaid dimeric joint chain is provided according to FIG. 1.

What is claimed is:

1. An artificial joint for use as an endoprosthesis for replacing a natural joint, said artificial joint comprising at least two artificial joint members each having curved articulation faces;

wherein said joint is a flat or spherical four joint comprising first and second sides on opposite sides of a mid-plane;

wherein on each side of the joint a curved contact boundary is formed on each of the articulation faces; the curved contact boundary on one of the articulation faces being part of an elliptical section contour of a first cylinder or cone representing a fixed joint member, and the curved contact boundary on the other of said articulation faces having the form of a counter track of a second cylinder or cone representing a moved joint member which rolls or slides on the first cylinder or cone;

each side of said joint having a fixed or moving holoid lying in a reference plane or sphere, said reference plane or sphere being selected such that it lies between the condyles to be constructed;

wherein a straight contact line along which the fixed and moved members touch at any given instant is drawn from a respective contact point lying on the curved contact boundaries either to a point which is fixed relative to the fixed or moved member and which lies in a randomly selected sagittal plane shifted toward the interior of the joint, or to the instantaneous center of revolution on the fixed or moving holoid; and wherein the sum of the straight contact lines forms a first contact face on the fixed member and a second contact face on the moved member, said first and second contact faces each representing a joint face of one of the two sides of the four-joint.

2. An artificial joint according to claim 1, wherein the curved contact boundary on one of the articulation faces is part of an elliptical section contour of a first cylinder having a radius R1 and the curved contact boundary on the other of said articulation faces is a counter track of a second cylinder having a radius R2, and wherein the first and second cylinders are arranged with respect to each other such that they form a stretched dimeric link chain having an axial path radius R which satisfies the relationship R=R2+R1 or an overlapped dimeric link chain having an axial path radius R which satisfies the relationship R=R2−R1.

3. An artificial joint according to claim 1, wherein the curved contact boundary on one of the articulation faces is part of an elliptical section contour of a first cone having a cone angle $\alpha 1$, the curved contact boundary on the other of said articulation faces is a counter track of a second cone having a cone angle $\alpha 2$, and wherein the first and second cones are arranged with respect to each other such that they form a stretched dimeric link chain having an angle $\alpha$ which satisfies the relationship $\alpha=\alpha 2+\alpha 1$ or an overlapped dimeric link chain having an angle $\alpha$ which satisfies the relationship $\alpha=\alpha 2-\alpha 1$.

4. An artificial joint according to claims 1, wherein the straight contact lines have curved extensions on the side of the curved contact boundaries opposite the contact faces such that toric surfaces are formed; said curved extensions lying in a plane defined by the respective straight contact line and a line perpendicular to a tangent (t) of the curved contact boundary at the respective contact point, and wherein the toric surfaces are formed such that outer portions of the articulation faces of the toric surfaces have no contact with each other.

5. An artificial joint according to claim 1, wherein said joint comprises an overlapped dimeric link chain forming a medial joint compartment of an artificial joint for a human knee, and a stretched dimeric link chain forming a lateral joint compartment of said artificial joint, and wherein the respective joint compartments comprise femur-side joint parts and tibia-side joint parts which are rigidly connected with respect to each other.

* * * * *